US006852502B1

(12) United States Patent
Martin

(10) Patent No.: US 6,852,502 B1
(45) Date of Patent: Feb. 8, 2005

(54) ELECTROCHEMILUMINESCENT ENZYME BIOSENSORS

(75) Inventor: Mark T. Martin, N. Bethesda, MD (US)

(73) Assignee: BioVeris Corporation, Gaithersburg, MD (US)

( * ) Notice: Subject to any disclaimer, the term of this patent is extended or adjusted under 35 U.S.C. 154(b) by 1826 days.

(21) Appl. No.: 08/467,712

(22) Filed: Jun. 6, 1995

(51) Int. Cl.[7] .............................. C12Q 1/26; C12Q 1/32
(52) U.S. Cl. .......................................... 435/25; 435/26
(58) Field of Search .............................. 435/29, 25, 26

(56) References Cited

U.S. PATENT DOCUMENTS

| | | | |
|---|---|---|---|
| 5,061,455 A | 10/1991 | Brose et al. | |
| 5,068,088 A | 11/1991 | Hall et al. | |
| 5,093,268 A | 3/1992 | Leventis et al. | |
| 5,147,806 A | 9/1992 | Kamin et al. | |
| 5,221,605 A | 6/1993 | Bard et al. | |
| 5,229,202 A | 7/1993 | Tomono et al. | |
| 5,235,808 A | 8/1993 | Taylor | |
| 5,250,415 A | 10/1993 | Ebeling et al. | |
| 5,264,092 A | 11/1993 | Skotheim et al. | |
| 5,310,687 A | 5/1994 | Bard et al. | |
| 5,324,835 A | 6/1994 | Yamaguchi et al. | |
| 5,340,722 A | 8/1994 | Wolfbeis et al. | |
| 5,384,028 A | 1/1995 | Ito et al. | |
| 5,527,710 A | * 6/1996 | Nacamulli et al. | .......... 436/517 |

OTHER PUBLICATIONS

Biosensor Design and Application edited by Paul R. Mathewson an John W. Finley, published in 1992, American Chemical Society, Washington, D.C.
Dixon and Webb, The Enzymes, Academic Press 684–702 (1979).
Plapp, 248, Journal of Biological Chemistry, 3470–3475 (1973).
Leland and Powell "Electrogenerated Chemiluminescence: An Oxidative–Reduction Type ECL Reaction Sequence Using Tripropyl Amine," 137, J. of the Electrochemical Society, 3127–3129 (1990).
Blackburn et al. "Electrochemiluminescence Detection for Development of Immunoassays and DNA Probe Assays for Clinical Diagnostics," 37, Clinical Chemistry, 1534–1539 (1991).
Persson et al. "Continous Regeneration of NAD(H) Covalently Bound to a Cysteine Genetically Engineered Into Glucose Dehydrogenase," 9, Bio/Technology, 280–284 (1991).
Mansson and Mosbach, 136, Methods in Enzymology, 3–34 (1987).
Yomo et al. "Preparation and Kinetic Properties of 5–Ethylphenazine–glucose–dehydrogenase–NAD+ Conjugate, Semisynthetic Glucose Oxidase," 200, European Journal of Biochem., 759–766 (1991).
Bozler et al. "Synthesis and Applicationof a Fluorescent Imido Ester for Specific Labelling of Amino Groups in Proteins," 749, Biochimica et Biophysica Acta, 238–243 (1983).
Yang et al. "Electrochemiluminescence: A New Diagnostic and Research Tool," 12, Bio/Technology, 193–194 (1994).
Manssson et al. "Covalent Binding of an NAD Analogue to Liver Alcohol Dehydrogenase Resulting in an Enzyme-Coenzyme Complex not Requireing Exogenous Coenzyme for Activity," 86, European Journal of Biochemistry, 455–463 (1978).
Branden et al. "Edhydrogenases," 36, Experientia Supplemental, 62–63.
Massey, Biomedical Products, (Oct. 1992) (not included).
Biosensor Design and Application edited by Paul R. Mathewson and John W. Finley, published in 1992, American Chemical Society, Washington, D.C. (not included).
Dixon and Webb, The Enzymes, Academic Press 684–702 (1979) (not included).
Plapp, 248, Journal of Biological Chemistry, 3470–3475 (1973) (not included).

* cited by examiner

*Primary Examiner*—George C. Elliott
*Assistant Examiner*—Jon D. Epperson
(74) *Attorney, Agent, or Firm*—Finnegan, Henderson, Farabow, Garrett & Dunner, L.L.P.

(57) ABSTRACT

Electrochemiluminescent enzymes, their preparation and use as biosensors are disclosed. Specifically, two appendages are covalently attached to a desired dehydrogenase enzyme; (1) a nicotinamide adenine cofactor or analog thereof, and (2) a luminescent ruthenium complex. For example, glucose concentrations is the following way. A doubly-modified glucose dehydrogenase could oxidize glucose with concomitant reduction of the attached $NAD^+$ to NADH. Because NADH, but not $NAD^+$, is able to interact with surface ruthenium to promote ECL, only enzyme molecules that have reacted with glucose will emit light from their ruthenium label in an ECL instrument. The relative close proximity of NADH and ruthenium on the enzyme surface enhances light emission as compared to the same concentrations in free solution. When NADH reduces ruthenium, it returns to become $NAD^+$, permitting multiple cycles of ECL light emission from a single enzyme molecule. Such biosensors can be used in solution or bound to a solid surface. Assays employing the biosensor molecules can be performed on an IGEN Origen[R] Analyzer.

6 Claims, No Drawings

ELECTROCHEMILUMINESCENT ENZYME BIOSENSORS

BACKGROUND OF THE INVENTION

1. Field of the Invention

The technical field is analytical biochemistry, especially as pertains to diagnostics. More specifically, the invention involves the preparation and use of novel enzyme-based biosensors which blend the useful properties of a tailored dehydrogenase with electrochemiluminescence (ECL) based assay format to detect and the quantify a specific analyte or analytes using conventional biosensor arrangements.

2. Background Information

Biosensors contain biomolecules, such as enzymes or antibodies, or whole-cell testers. Biosensors can be used for rapid, real-time detection of materials in environmental and/or clinical samples. The present biosensor invention involves the creation of enzyme-coenzyme-electrochemiluminescence tagged conjugates. Their development reflects a multidisciplinary effort. The background of the relevant technological areas will be discussed sequentially.

Assays based on electrochemiluminescence (ECL) are well known in the art and are finding expanding applications because of their accuracy, ease of use and freedom from radioactive materials.

A particularly useful ECL system is described in a paper by Yang et al, *Bio/Technology*, 12, pp. 193–194 (February 1994). See also a paper by Massey, *Biomedical Products*, October 1992 as well as U.S. Pat. Nos. 5,235,808 and 5,310,687, the contents of these papers and patents being incorporated herein by reference.

ECL processes have been demonstrated for many different molecules by several different mechanisms. In Blackburn et al (1991) *Clin.Chem.* 37/9, pp. 1534–1539, the authors used the ECL reaction of ruthenium (II) tris (bipyridyl), $Ru(bpy)_3^{2+}$, with tripropylamine (TPA) (Leland et al (1990) *J. Electrochem. Soc.* 137:3127–31) to demonstrate the technique. Salts of $Ru(bpy)_3^{2+}$ are very stable, water-soluble compounds that can be chemically modified with reactive groups on one of the bipyridyl ligands to form activated species with which proteins, haptens, and nucleic acids are readily labeled. The activated form of the Ru(bpy)$_3^{2+}$ used by Blackburn et al was $Ru(bpy)_3^{2+}$-NHS ester:

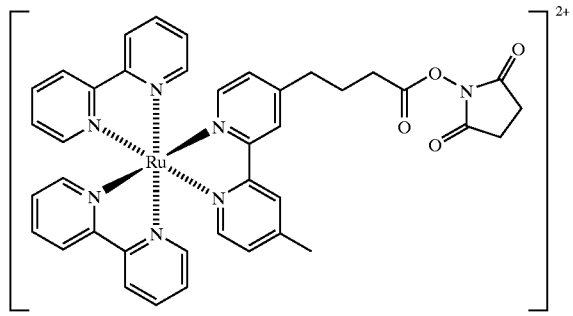

The creation of tailored enzyme conjugates is a developing area, especially in the clinical biochemical area. Ebeling et al. (U.S. Pat. No. 5,250,415) utilized recombinant techniques to enhance the quality and stability of NAD/NADP and dependent glucose dehydrogenase (E.C. 1.1.1.42). Through the use of recombinant techniques, isoenzymes were produced in high quality and the enzymes display comparable stability over the range of temperatures between 20° and 50° C. The enzymes are disclosed as suitable for use as medical diagnostic applications.

The creation of semi-synthetic glucose oxidase involving the formation of enzyme conjugates having linked regenerative moieties has been attempted by certain research groups with some success. See Yomo et al., "Preparation and Kinetic Properties of 5-ethylphenazine-glucose-dehydrogenase-NAD$^+$ conjugate, A Semi-Synthetic Glucose Oxidase," *European J. Biochem.* (Germany), (Sep. 15, 1991), Vol. 200(3), pp. 759–66. 5-ethylphenazine-glucose-dehydrogenase-NAD$^+$ conjugate (EP(+)-Glc DH-NAD$^+$) was prepared by linking both poly (ethylene glycol)-bound 5-ethyl-phenazine and poly (ethylene glycol)-bound NAD$^+$ to glucose dehydrogenase. This conjugate is a semi-synthetic enzyme having glucose oxidase activity using oxygen or 3-(4,5-dimethyl-2-thiazoyl)-2, 5-diphenyl-2l t-tetra zolium bromide (MTT) as an electron acceptor. The semi-synthetic oxidase has two catalytic steps: reduction of the NAD$^+$ moiety by the active site of the glucose dehydrogenase moiety and oxidation of the NADH moiety by another catalytic site of the ethylphenazine moiety.

The selective labelling of amino groups in proteins such as beta-D-glucose: NAD(P+) 1-oxidoreductases (EC 1.1.1.47) has been demonstrated. Bozler et al. (Biochim. Biophys. Acta, Vol.749, No. 3, pp. 238–43) selectively labelled glucose dehydrogenase at a lysine group with (2-5$^1$-dimethyl amino naphthalene-1-sulfonamido) methylamidic acid methyl ester. The ester was synthesized for the purpose of fluorescence labelling of amino groups of proteins. The incorporation of the dansyl group served as an extrinsic fluorescent probe which can be determined spectrophotometrically.

Biosensors are continually growing area of technology. The term biosensor encompasses a wide range of technologies and reflects multi-disciplinary efforts. There is a continuing need in this area for the enhancement of sensitivity, reliability and rapidity.

A common thread to biosensor technology is the use of a biological material in the measurement of analyte. This is a rather encompassing definition.

A representative text in this field, illustrating the blend of technologies, is *Biosensor Design and Application*, edited by Paul R. Mathewson and John W. Finley, which was published in 1992 by American Chemical Society, Washington, D.C.

Biosensors, in addition to the requisite biological molecule, can include a variety of measuring systems, e.g. an electrode system comprising a measuring electrode and a luminescence counter wherein the reaction layer contacts the electrode system. The reaction layer typically comprises one molecule electron acceptor, a measuring enzyme and chemiluminescent sensor. The diversity of biosensor systems is evidenced by the devices such as those illustrated in U.S. Pat. Nos. 5,324,835, 5,229,202 and 5,384,028.

Glucose biosensor giving stable measured results without NAD consumption are known. Such biosensors are useful for the qualitative or quantitative determination of one or more components in a liquid mixture by electrochemical regeneration of coenzyme. Typically, such an electrode comprises a redox polymer adsorbed on the surface of the electrode, one or more enzymes wherein at least one is a dehydrogenase and a coenzyme such as NADH, NADPH or their analogues. See Gordon et al, U.S. Pat. No. 5,264,092.

Another approach is evidenced in U.S. Pat. No. 5,340,722 (Wolfbeis et al.) which teaches a continuous and reversible determination using a biosensor which involves a flavin co-enzyme (FMN, FAD), oxidases and oxygenases. The assay is fluorescence based. During enzymatic oxidation the co-enzyme simultaneously transitions into a reduced form, which is then immediately reconverted into the oxidized form by means of oxygen. The transition from oxidized form to reduced form is linked to a change in fluorescence properties, which serve as the analytical parameter.

However, there still remains a need to further enhance the economy, reliability, sensitivity and responsiveness of biosensors.

SUMMARY OF THE INVENTION

Broadly stated, the invention contemplates an electrochemiluminesence based assay using a biosensor having a dehydrogenase which has been modified to properly position TAG and the desired nucleotide cofactor (coenzyme) near the active site. Such positioning enhances reaction times improves the energy efficiency of the system which improves accuracy, speed and reliability and the like for the detection of enzymes or their substrates and cofactors.

The object of the invention is to both enhance sensitively and specificity of ECL-based assays and to conserve reagent usage.

The monitored or detected analyte is either the substrate of a dehydrogenase or a substance that can be converted into the substrate of a dehydrogenase. The dehydrogenase is the molecule that allows sensing of the analyte by an ECL instrument. It is also envisioned that the biosensor molecule of the invention can be used in conjuction with another enzyme or enzyme system which produces a product which is measured by the biosensor molecule. This would further increase the range of applications.

The dehydrogenase is not present in its natural form, but rather has been chemically-modified so that it has two unnatural appendages. One appendage is a covalently attached functional analog of $NAD(P)^+$, $NAD(P)H$. Such enzymes have been made (Persson et al. 1991). This nicotinamide cofactor is specifically attached in a way that it can bind in the active site of the enzyme and function as a redox reagent as part of the natural enzyme mechanism. The second appendage is an ECL label such as a derivative of $Ru(bpy)_3^{2+}$. Such proteins have been made (Blackburn et al. 1991).

The way that the biosensor works is as follows:
(1) The analyte is oxidized by the $NAD^+$ form of the doubly-modified enzyme, causing the enzyme to be converted to the NADH form.
(2) In an ECL instrument, voltage will be applied to the enzyme, causing the NADH appendage to become oxidized by donating an electron to the luminescent ruthenium-containing appendage, which in turn emits light (Downey et al. 1992). As a result, NADH returns to become $NAD^+$ such that a second molecule of analyte can be oxidized and the cycle can be repeated. The demonstration of electron transfer through ruthenium-labelled proteins has previously been accomplished (Pan et al. 1993; Wuttke et al.)

Some analytes (and their enzymes) that function in the above mechanism are: glucose (glucose dehydrogenase), ethanol (alcohol dehydrogenase), and lactate (lactate dehydrogenase). It is envisioned, however, that other oxidoreductases such as those listed on pages 684–702 of the *Enzymes* (Academic Press (1979)) by M. Dixon and E. C. Webb could also be utilized. Their selection depends on the location of amino acids near the active site with sidechains which could be linked to either NAD or TAG moities through an appropriate linking group, e.g. ester, thiol ether, etc.

The main advantages of this invention are:
(1) potential high sensitivity and low background. The fixed nature of the reagents (on a single molecule) is desirable because of entropic effects; their effective concentrations relative to each other will be very high which will give substantially better yields (of light) than if they were free in solution.
(2) possibly lowered analysis cost over the same system in which the enzyme, NADH, and the ruthenium compound are free in solution. Because of this, lower concentrations of the reagents will give results equivalent to results obtained with free reagents, and also because one NADH molecule can be recycled, the cost of analysis will be reduced.
(3) combining three reagents into one molecule is more attractive for immobilized systems. It would be extremely attractive to be able to immobilize biosensors so that they can be reused. If the enzyme alone were immobilized, the other reagents (NADH and $Ru(bpy)_3^{2+}$) would need to be added for each analysis. In this invention, all reagents could be immobilized in a way in which would be functional.

Devices employing biosensor molecules typically employ the molecule in an immobilized state. Immobilization provides stability to the molecule and ensures its continued presence in a desired area of the device for optimal performance. Typical of the techniques used to immobilize the biosensor molecules of this invention are those disclosed on pages 3 through 34 of *Methods of Enzymology*, Vol. 136 (1987).

At the present time, a preferred use for the glucose dehydrgenase of the invention is as a glucose biosensor. Functional glucose dehydrogenase has been made which has an immobilized NADH molecule (Persson et al., 1991). This modified enzyme could be reacted with $Ru(bpy)_3^{2+}$-NHS ester (IGEN, Inc., Rockville, Md.) by conventional means used to attach this compound to surface lysines present on antibodies (Blackburn et al., 1991). Such modification may result in one or more ruthenium appendages (multiple appendages are acceptable or even advantageous if the enzyme remains active). The doubly-modified enzyme could be purified by dialysis or chromatography. Addition of glucose followed by testing in the ECL instrument (conventional analysis for NADH), would give a light signal depending on the activity of the enzyme, which in turn depends on the glucose concentration.

The improvements of the invention over the prior art are set forth above. They include sensitivity, cost, and ease of immobilization. Higher sensitivity (over comparable assays in which ruthenium and the nicotinamide cofactor are not attached to the dehydrogenase) results from advantages relating to the intramolecular nature of the electron transfer (Pam Liang and Mark Martin, unpublished ECL results). Cost savings will result from the reusable nature of the doubly-modified enzyme (easier recovery as opposed to recovery and reuse of the free enzyme, ruthenium complex, and nicotinamide cofactor). Finally, it would be impractical to separately immobilize all three components on a solid surface in a functional way. Coupling all three into one functional molecule allows solid phase immobilization (and hence convenience and reduce cost, compared to having enzyme, ruthenium, and cofactor free in solution).

Procedures for making NAD-labelled glucose dehydrogenase are known. Since dehydrogenases are a fairly conserved group of enzymes, similar methods could be used with other dehydrogenases. Procedures for labelling proteins (usually antibodies) with $Ru(bpy)_3^{2+}$-NHS ester (through lysins) are also well known (IGEN, Inc. technical notes).

The enzyme biosensor of the invention requires for use an ECL instrument and a solution containing analyte, such as glucose. A solution containing analyte (such as glucose) would be appropriately diluted, if necessary, and mixed in solution with enzyme biosensor. There are at least two ways the analyte could be measured; after fractional enzyme turnover and by rate measurements in the ECL instrument. For the fractional enzyme turnover method the ECL would be measured after a defined time period, less than the time required for all enzyme molecules to complete one turnover. If analyte concentration and time are appropriately adjusted, less than 100% of the enzyme molecules would have reacted with glucose, and less than maximal ECL would be generated. Based on the established kinetic parameters for the reaction, glucose concentration could be determined. Alternatively, analyte concentration could be determined by rate measurements in the instrument. The enzyme reaction could be carried out at the same time the ECL reaction is in progress (such as by pulsing of voltage), so that NADH would be actively recycled and a rate measurement could be made.

The same system could be used without covalently attaching the reagents. Alternatively, a non-ECL system could be used without ruthenium (free enzyme and free NAD $(P)^+$), where the UV absorbance of generated NAD(P)H could be monitored spectrophotometrically.

Novel NAD(P)H-like compounds could be used that are enzymatically active and also ECL active. Also, non-ruthenium ECL-active lumiphores could be used in place of $Ru(bpy)_3^{2+}$).

DETAILED DESCRIPTION OF THE INVENTION

Mechanism of ECL excitation is as follows. Analyte is oxidized in the presence of the biosensor molecule of the invention which causes the $NAD^+$ containing appendage to be converted to NADH. $Ru(bpy)_3^{2+}$ (TAG) and NADH are oxidized at the surface of a gold electrode, forming $Ru(bpy)_3^{3+}$ and $NADH^+$., respectively. (In this description, $NAD^+$ and TAG are covalently attached to the dehydrogenase.) The $NADH^+$. spontaneously loses a hydrogen, forming NAD.. The NAD., a strong reductant, reacts with $Ru(bpy)_3^{3+}$, a strong oxidant, forming the excited state of the detectant, $Ru(bpy)_3^{2+}$. The excited state decays to the ground state through a normal fluorescence mechanism, emitting a photon having a wavelength of 620 nm.

Organic compounds which are suitable electrochemical detectants include, for example, rubene and 9,10-diphenyl anthracene. Many organometallic compounds are suitable electrochemical detectants, but of preferable use are Ru-containing compounds, such as ruthenium II tris-bipyridine chelate, and Os-containing compounds. Detectants useful in the presently disclosed invention can be found in U.S. Pat. No. 5,310,687, the contents of which are incorporated herein by reference.

These detectants are stable for long periods. In addition, the detectants are safe and relatively inexpensive. They give a highly characteristic signal and do not occur in nature. Measurements based on luminescence of such detectants are sensitive, fast, reproducible and utilize simple instrumentation. The signal is generated repeatedly by each molecule of the detectant, thereby enhancing the sensitivity with which these detectants may be detected. The preferred electrochemiluminescent detectants of the present invention are conveniently referred to herein as $Ru(bpy)_3^{2+}$. Various amounts of this detectant, or its equivalent, may be employed.

It is also to be noted that these detectants can be used directly in biological or food samples without pretreatment of sample.

The energy necessary for formation of the excited state arises from the large difference in electrochemical potentials of the $Ru(bpy)_3^{3+}$ and NAD.. The excited-state $Ru(bpy)_3^{2+*}$ decays through a normal fluorescence mechanism, emitting a photon at 620 nm. This process regenerates the original form of the $Ru(bpy)_3^{2+}$, which is free to cycle multiple times through the reaction sequence. Each ECL-active detectant, therefore, can emit many photons during each measurement cycle, thereby enhancing detection.

Quantification of the $Ru(bpy)_3^{2+}$ detectant can be readily automated with relatively uncomplicated instrumentation. The heart of an instrument is the electrochemical flow-cell, containing the working electrodes and counter electrodes for initiation of the ECL reaction. Both of the electrodes are fabricated from gold, but other materials have been used with various degrees of success. A potentiostat applies various voltage waveforms to the electrodes, and a single photomultiplier tube (PMT) detects the light emitted during the ECL reaction. An Ag/AgCl reference electrode is placed in the fluid path downstream from the flow cell, and a peristaltic pump is used to draw various fluids through the flow cell. In a typical sequence, the assay fluid is drawn from a test tube into the flow cell and the detectant is quantified by applying a ramp voltage to the electrodes and measuring the emitted light. After the measurement, a high-pH cleaning solution is drawn into the cell for an electrochemical cleaning procedure. A conditioning solution is then drawn into the cell, and a voltage waveform is applied that leaves the surfaces of the electrodes in a highly reproducible state, ready for the next measurement cycle.

The ECL reaction can be efficiently initiated by many different voltage waveforms. Measurements of the working electrode current and the ECL intensity are induced by the application of a triangle wave to the electrodes. The applied voltage as shown is actually the voltage measured at the Ag/AgCl reference electrode and includes the effects of a significant uncompensated resistance; consequently, the actual voltage applied at the working electrode is substantially less than that depicted. The triangle waveform rises from 565 to 2800 mV at a rate of 750 mV/s and then decreases at the same rate to 1000 mV. The current that flows in the cell is primarily the result of the oxidation of the analyte and the hydrolysis of water. Oxidation of both the analyte and $Ru(bpy)_3^{2+}$ becomes evident when the applied voltage reaches ~1100 mV and produces a luminescence. The intensity of the luminescence increases with the applied voltage until the analyte at the surface of the electrode is depleted, resulting in decreased intensity. The intensity of the observed luminescence is great enough that it can easily be measured with conventional PMTs operating either in photon-counting or current modes.

After the sample is contacted with the biosensor, the ECL measurement is performed by application of electrical potential to the working electrode. This gives a characteristic signal from the emitted light. Relatively little interference results from background presented by the other materials present in the sample or added buffer.

Accordingly, the apparatus and methodology suitable for the performance of the process of this invention include, as noted earlier, those shown in U.S. Pat. Nos. 5,068,088, 5,061,455, 5,093,268, and 5,147,806 and 5,221,605, which patents are expressly incorporated herein by reference. In addition, electrochemiluminesence molecules for use in the measuring system as detectants include those bidentate aromatic heterocyclic nitrogen-containing ligands of ruthenium and osmium described in U.S. Pat. Nos. 5,310,687 and 5,310,687, which patents are expressly incorporated herein by reference.

Reagent kits containing the materials necessary for the performance of the assays can be assembled to facilitate handling, and foster standardization. Materials to be included in the kit may vary depending on the ultimate purpose. Typically the kit would include the modified enzyme mutein conjugate labelled at or near the active site with cofactor and TAG, necessary buffers, and standards. The kit may also include a measuring or detecting enzyme system depending upon application. The standards can be chemical reagents or data (empirical) in printed or electronic form necessary for the calibration necessary for performance of the assay.

EXAMPLE 1

Preparation of an NAD$^+$-Alcohol Dehydrogenase-Ru(bpy)$_3^{2+}$ Conjugate

Bioconjugates can be made in which dehydrogenases are covalently linked to both an NAD$^+$ analog and a derivative of Ru(bpy)$_3^{2+}$. In these cases, the enzyme is not a mutant protein but rather is the naturally-occurring enzyme molecule. Use of the naturally-occurring enzyme has the advantage that no mutagenesis is required in order to prepare the conjugate. On the other hand, in some cases, preparation of a mutant enzyme may be preferred or essential because of unsatisfactory positioning of the natural amino acid sidechains that react with the NAD$^+$ analog or the Ru(bpy)$_3^{2+}$ derivative. The natural amino acids that react with the NAD$^+$ or Ru(bpy)$_3^{2+}$ derivatives may be absent or not properly positioned for either the enzyme reaction (requiring appropriate positioning of the NAD$^+$ analog relative to the enzyme active site) or the ECL reaction (requiring appropriate positioning of the Ru(bpy)$_3^{2+}$ derivative relative to the NAD$^+$ analog).

Part 1: Preparation of the NAD-ADH Conjugate (based on M. -O. Månsson, et al., *Eur. J. Biochem.* 86, 455–463 (1978)).

ADH (equine liver alcohol dehydrogenase, Sigma Chemical Co., St. Louis, Mo.) will be dialyzed into 50 mM triethylamine, pH 7.5. To 5 mg of the dialyzed enzyme in 1.3 mL triethylamine buffer (40° C.) (enzyme concentration about 0.1 mM) will be added that NAD$^+$ analog (N6-([6-aminohexyl]-carbamoylmethyl)-nicotinamide adenine dinucleotide, lithium salt, Sigma Chem. Co.) to a final concentration of 5 mM. Pyrazole (Sigma Chem. Co.) will be added to the solution to a concentration of 10 mM. (Pyrazole stabilizes the enzyme-NAD$^+$ complex so it can react (C. Woenckhaus et al., Bioorg. Chem. 12, 45–57 (1983).) The coupling agents, 1-ethyl-3(3-dimethyl-aminopropyl)-carbodiimide (EDC) and N-hydroxysuccinimide (NHS) will then be added in 500-fold and 250-fold molar excesses (compared to enzyme subunit concentration, the enzyme is a dimer). EDC will be added in four equal portions at 12 hour intervals and NHS in two equal portions at 0 and 12 hours. The mixture is reacted for 48 hours, during which time the pH is kept at 7.5 using additions of NaOH. After reaction for 48 hours, the solution will be dialyzed overnight against 3.0 L of 50 mM glycine, 50 mM sodium bicarbonate, pH 7.5. The solution will then be dialyzed three times (at least 6 hours each time) against 3 L of 50 mM bicarbonate, pH 8.0.

Part 2: Preparation of an NAD-ADH-Ru(bpy)$_3^{2+}$ Conjugate (based on B. L. Plapp et al., J. Biol. Chem. 248, 3470–3475 (1973))

To the solution of the NAD-ADH conjugate prepared above (in 50 mM NaHCO$_3$, pH 8.0) pyrazole will be added to a final concentration of 10 mM and (normal) NAD$^+$ will be added to a final concentration of 2 mM. Amino groups outside of the active site will be acetimidylated by adding 2.1 M ethyl acetimidate-HCl (Sigma Chem. Co.) (volume will be added to increase enzyme solution by 5%). (Stock solution of 2.1 M ethyl acetimidate will be made up fresh and pH adjusted to 8.0). The reaction will be allowed to go for one hour at 25° C., then three more additions of ethyl acetimidate will be made hourly (total reaction time=4 hours). The protein will then be dialyzed extensively, against 33 mM sodium phosphate, 0.5 mM EDTA, 2.0 mM adenosine monophosphate, pH 8.0, then against 0.2 M sodium bicarbonate, pH 8.0. The external lysine-protected NAD-ADH will be reacted with an NHS ester derivative of Ru(bpy)$_3^{2+}$ (IGEN, Inc., Gaithersburg, Md.) by established means. Unreacted (free) Ru(bpy)$_3^{2+}$ will be removed by dialysis against a neutral buffer. By comparison with literature reports only one Ru(bpy)$_3^{2+}$ per enzyme subunit will be incorporated, on Lys 228 (See Brändén et al., Experientia Supplemental 36, J. Jeffrey, ed., Dehydrogenases, pp. 62–3.).

EXAMPLE 2

Assays of NAD$^+$-ADH-Ru(bpy)$_3^{2+}$ Catalytic Activity

Assays 1 and 2 are based on M. -O. Månsson, et al., Eur. J. Biochem. 86, 455–463 (1978). Assay 3 is the electrochemiluminescent assay in which enzymatic conversion of ethanol by the NAD$^+$-ADH-Ru(bpy)$_3^{2+}$ conjugate is accompanied by light emission.

Assay 1 Spectrophotometric, Non-Regenerating Assay

This assay will reduce immobilized NAD$^+$ analog to the NADH analog. The reverse reaction will not occur (the assay is non-regenerating). The absorbance increase at 340 nm will indicate the concentration of immobilized NAD$^+$ analog ($\Delta\epsilon_{340}$=6220 M$^{-1}$cm$^{-1}$).

In a cuvette, enzyme will be added ($\leq$1 mM) to 0.1 M sodium phosphate buffer (pH 7.2) containing 12 mM semicarbazide (Sigma Chem. Co.). The solution will be equilibrated at 25.0±0.1° C. Concentrated ethanol (final concentration=500 $\mu$M) is added in a small volume. The total absorbance change at 340 nm will be measured.

Assay 2 Spectrophotometric, Regenerating Assay

This assay will continually recycle immobilized NAD$^+$/NADH on the surface of the enzyme conjugate (NAD$^+$-ADH-Ru(bpy)$_3^{2+}$). ADH itself will reduce NAD$^+$ to NADH upon oxidation of ethanol to acetaldehyde. A second enzyme, diaphorase (Sigma Chem. Co.), will be added which will convert NADH-ADH-Ru(bpy)$_3^{2+}$ back to NAD$^+$-ADH-Ru(bpy)$_3^{2+}$.

To assay for functional NAD$^+$-ADH-Ru(bpy)$_3^{2+}$, the following solutions will be mixed in a cuvette, 200 $\mu$L 0.5 M Tris (pH 8.5), 100 $\mu$L 0.1% gelatin (in water, filtered), 10 $\mu$L 30 mM INT-Violet (in 10 mM phosphate buffer, pH 7.5, 10% DMSO, and 0.01% filtered gelatin), 10 $\mu$L diaphorase (10 mg/mL in 10 mM phosphate, pH 7.5), 30 $\mu$L ADH (or NAD-ADH or NAD-ADH-Tag), 650 μL 100 μM ethanol. The absorbance of the mixture is continuously read in a spectrophotometer at 490 nm.

Assay 3 Electrochemiluminescent Assay

The assay is performed similarly to Assay 1 (above). However, instead of measuring the absorbance increase when ethanol is added, similar enzyme conjugate solutions (with and without added ethanol) will be measured in an IGEN ECL Analyzer (IGEN, Inc., Gaithersburg, Md.). In the absence of ethanol the enzyme conjugate will be in the form $NAD^+$-ADH-Ru(bpy)$_3^{2+}$ (non-electrochemiluminescent). Following enzymatic conversion of ethanol to acetaldehyde, the enzyme conjugate will be in the form NADH-ADH-Ru (bpy)$_3^{2+}$ (electrochemiluminescent). Moreover, voltage is applied to the enzyme conjugate in the ECL instrument, light is emitted, and the conjugate returns to the original form ($NAD^+$-ADH-Ru(bpy)$_3^{2+}$). This original form can then catalyze oxidation of another molecule of ethanol, which would convert the enzyme conjugate once against to the electrochemiluminescent NADH form. Thus, multiple photons can be generated by the enzyme conjugate in the presence of ethanol.

EXAMPLE 3

Preparation of a $NAD^+$-Zutant Glucose Dehydrogenase-Ru (bpy)$_3^{2+}$

In this example, a glucose dehydrogenase mutant will be prepared to contain a strategically-located surface sulfhydryl group which can react with an $NAD^+$ analog to produce an $NAD^+$-enzyme conjugate. The mutation is positioned so that the tethered $NAD^+$ molecule can bind to the $NAD^+$ binding site in the enzyme and be enzymatically efficiently reduced to NADH. The mutant glucose dehydrogenase-$NAD^+$ conjugate will then be reacted with an N-hydroxysuccinimide (NSH) derivative of Ru(bpy)$_3^{2+}$ to yield a doubly-modified enzyme; $NAD^+$-GlcDH-Ru(bpy)$_3^{2+}$. This enzyme conjugate will be luminescent in an ECL instrument. For every glucose molecule that the enzyme catalyzes, the surface $NAD^+$ will be converted to NADH. In an ECL instrument (IGEN, Inc., Gaithersburg, Md.), NADH but not $NAD^+$ will cause enzyme surface-immobilized Ru(bpy)$_3^{2+}$ to emit a photon of light. Thus, a molecule of glucose will result in a photon of light to be emitted by the doubly-modified enzyme. Moreover, in the ECL process, NADH is reconverted to $NAD^+$. Thus, the doubly-modified enzyme is regenerated by emitting light and can be used repeatedly.

Part 1 Preparation of the Mutant GlcDH.

Mutant GlcDH has been previously prepared by site-directed mutagenesis (M. Persson, et al., Bio/Technology (1991) 9,280–284). The residue asp$^{44}$ in glucose dehydrogenase was mutated to a cys$^{44}$ by standard mutagenesis protocol. The mutant protein (GlcDHcys$^{44}$) was expressed in E. coli and purified by conventional means.

Part 2 Preparation of a Cysteine-Reactive $NAD^+$ Derivative.

A thiol reactive $NAD^+$ analog has been prepared (M. Persson, et al., Bio/Technology (1991) 9, 280–284). Essentially, the method involves reaction of two commercially-available reagents; N-succinimidyl-3-[2-pyridyldithio]propionate (SpDP; Pierce Chem. Co.) and N$^6$[6-aminohexyl-(carbamoylmethyl)-NAD (Sigma Chem. Co.). The resulting product will react with the GlcDHcys$^{44}$ to yield the desired $NAD^+$-modified enzyme. Such an $NAD^+$-labelled GlcDH has been prepared (M. Persson, et al., Bio/Technology (1991) 9, 280–284).

Part 3 Preparation of $NAD^+$-GlcDHcys$^{44}$-Ru(bpy)$_3^{2+}$

The $NAD^+$-GlcDHcys$^{44}$ molecule prepared in Part 2 will be reacted with an NHS ester derivative of Ru(bpy)$_3^{2+}$ (IGEN, Inc.) using established protocols (0.2 M NaHCO$_3$, pH 8.0, room temperature) for reactions of this reagent with proteins (IGEN technical notes). One or more lysine residues on the surface of $NAD^+$-GlcDHcys$^{44}$ will be covalently linked to Ru(bpy)$_3^{2+}$ as a result of the reaction. Following the reaction, free unreacted Ru(bpy)$_3^{2+}$ will be removed by dialysis to yield $NAD^+$-GlcDHcys$^{44}$-Ru(bpy)$_3^{2+}$.

EXAMPLE 4

ECL Detection of Glucose Using $NAD^+$-GlcDHcys$^{44}$-Ru(bsy)$_3^{2+}$ $NAD^+$-GlcDHcys$^{44}$-Ru(bpy)$_3^{2+}$ will concurrently oxidize glucose to gluconolactone and reduce immobilized $NAD^+$ to NADH. Next, in an ECL instrument (IGEN, Inc., Gaithersburg, Md.), enzyme-immobilized NADH will efficiently cause neighboring immobilized Ru(bpy)$_3^{2+}$ to emit light. Thus, the doubly-modified enzyme will report the presence of glucose by emitting light.

In the test tube, enzyme ($NAD^+$-GlcDHcys$^{44}$-Ru(bpy)$_3^{2+}$) will be added ($\leq 1$ μM) to 0.1 M sodium phosphate buffer (pH 7.2). The solution will be equilibrated at 25.0±0.1° C. A glucose-containing solution is added in a small volume. In the absence of glucose the enzyme conjugate will be in the form $NAD^+$-GlcDHcys$^{44}$-Ru(bpy)$_3^{2+}$ (non-electrochemiluminescent). Following enzymatic conversion of glucose to gluconolactone, the enzyme conjugate will be in the form NADH-GlcDHcys$^{44}$-Ru(bpy)$_3^{2+}$ (electrochemiluminescent). Moreover, when voltage will be applied to the enzyme conjugate in the ECL instrument, light is emitted, and the conjugate returns to the original form ($NAD^+$-GlcDHcys$^{44}$-Ru(bpy)$_3^{2+}$). This original form can then catalyze oxidation of another molecule of glucose, which would convert the enzyme conjugate once again to the electrochemiluminescent NADH form. Thus, multiple photons can be generated by the enzyme conjugate in the presence of glucose.

Although the examples illustrate various modifications of the present invention, other variations will suggest themselves to those skilled in the art in light of the above disclosure. It is to be understood, therefore, that changes may be made in the particular embodiments described above which are within the full intended scope of the inventions as defined in the appended claims.

What is claimed is:

1. A method for the determination of the concentration of an enzyme substrate present in a specimen, comprising the steps of:

(a) contacting said specimen with an oxidoreductase conjugate under conditions which permit the oxidation of the enzyme substrate, said oxidoreductase conjugate comprising a co-factor and a species capable of generating an electrochemiluminescent signal separately linked in close proximity to an active site of said oxidoreductase in a manner which permits their electrochemical interaction with each other and a substrate also in close proximity to the active site;

(b) measuring the change in electrochemiluminescence from a base reading; and (c) determining the concentration of enzymatic substrate based on the measured change in electrochemiluminescent signal.

2. The method according to claim 1 wherein the measurement and determination is done on a real time basis.

3. The method according to claim 1 wherein the determination of enzymatic substrate is deduced from a comparison with established kinetic parameters for the reaction.

4. The method according to claim 1 wherein the determination of enzymatic substrate concentration is determined based on rate measurements in the instrument.

5. The method of claim 1 wherein the steps are carried out simultaneously.

6. The method of claim 5 wherein the voltage necessary for electrochemiluminescence is pulsed so as to actively recycle said co-factor and said species caDable of generating an electrochemiluminescent signal.

\* \* \* \* \*

UNITED STATES PATENT AND TRADEMARK OFFICE
CERTIFICATE OF CORRECTION

PATENT NO.    : 6,852,502 B1
DATED         : February 8, 2005
INVENTOR(S)   : Mark T. Martin It is certified that error appears in the above-identified patent and that said Letters Patent is hereby corrected as shown below:

<u>Column 12,</u>
Line 5, "caDable" should read -- capable --.

Signed and Sealed this

Tenth Day of May, 2005

JON W. DUDAS
*Director of the United States Patent and Trademark Office*